United States Patent
Saebo et al.

(10) Patent No.: US 6,333,353 B2
(45) Date of Patent: Dec. 25, 2001

(54) ISOMER ENRICHED CONJUGATED LINOLEIC ACID COMPOSITIONS

(75) Inventors: Asgeir Saebo, Oersta (NO); Carl Skarie, Detroit Lakes; Daria Jerome, Owatonna, both of MN (US)

(73) Assignee: Conlinco, Inc. (NO)

( * ) Notice: Subject to any disclaimer, the term of this patent is extended or adjusted under 35 U.S.C. 154(b) by 0 days.

(21) Appl. No.: 09/772,608

(22) Filed: Jan. 30, 2001

Related U.S. Application Data (63) Continuation of application No. 09/270,941, filed on Mar. 17, 1999, now Pat. No. 6,225,486, which is a continuation-in-part of application No. 09/072,422, filed on May 4, 1998, now Pat. No. 6,060,514, which is a continuation-in-part of application No. 09/072,421, filed on May 4, 1998, now Pat. No. 6,214,372.

(51) Int. Cl.$^7$ .................................................. A61K 31/20
(52) U.S. Cl. ........................ 514/558; 514/960; 514/962; 424/451
(58) Field of Search ................................. 514/558, 960, 514/962; 424/451

Primary Examiner—Deborah D. Carr
(74) Attorney, Agent, or Firm—Medlen & Carroll, LLP (57) ABSTRACT

Compositions and methods of using conjugated linoleic acid preparations enriched for the t10,c12 and c9,t11 isomers are disclosed. It is found that preparations of conjugated linoleic acid containing a ratio of t10,c12 to c9,t11 of about greater than 1.2:1 are desirable for a wide variety of nutritional, therapeutic and pharmacologic uses.

9 Claims, 2 Drawing Sheets

ISOMER ENRICHED CONJUGATED LINOLEIC ACID COMPOSITIONS

RELATED APPLICATIONS

This is a Continuation of application Ser. No. 09/270,941 filed on Mar. 17, 1999 now U.S. Pat. No. 6,225,086 which is a Continuation-in-Part of U.S. Ser. No. 09/072,422, filed May 4, 1998 now U.S. Pat. No. 6,060,519, and U.S. Ser. No. 09/072,421, filed May 4, 1998, now U.S. Pat. No. 6,214,372.

FIELD OF THE INVENTION

The present invention relates to the field of human and animal nutrition, and in particular to compositions containing conjugated linoleic acids (CLA).

BACKGROUND OF THE INVENTION

Conjugated linoleic acid (CLA) has become the focus of numerous research programs which seek to capitalize on its nutritional, therapeutic, and pharmacologic properties.

The rearrangement of the double bonds of linoleic acid to conjugated positions has been shown to occur during treatment with catalysts such as nickel or alkali at high temperatures, and during auto oxidation. Theoretically, eight possible geometric isomers of 9,11 and 10,12 octadecadienoic acid (c9,c11; c9,t11; t9,c11; t9,t11; c10,c12; c10,t12; t10,c12 and t10,t12) would form from the isomerization of c9,c12-octadecadienoic acid. A general mechanism for the isomerization of linoleic acid was described by J. C. Cowan in JAOCS 72:492–99 (1950). It is believed that the double bond is polarized by the result of a collision with an activating catalyst. The polarized carbon atom and its adjoining carbon are then free to rotate and the forces are such as to make the deficient carbon atom essentially planar. When the system then moves to relieve these forces set up as a result of the collision, both cis and trans isomers are formed. The formation of certain isomers of CLA is thermodynamically favored. This is due to the co-planar characteristics of the five carbon atoms around the conjugated double bond and a spatial conflict of the resonance radical. The relatively higher distribution of 9,11 and 10,12 isomers apparently results from the further stabilization of the c9,t11 or t10,c12 geometric isomers.

Advances in gas chromatography have enabled researchers to precisely determine the isomer composition of samples of CLA. In Christie et al., JAOCS 74 (11):1231 (1997), it was reported that the isomer distribution of a commercial sample of CLA was as follows: 8,10 (14%); 9,11 (30%); 10,12 (31%), and 11,13 (24%). In another study published by Christie et al. appearing in Lipids 33(2):217–21 (1998), the following CLA isomer composition of a commercial CLA preparation was reported: t11,t13 (0.74%); t10,t12 (1.23%); t9,t11 (1.18%); t8,t10 (0.46%); c11,t13 and t11,c13 (21.7%) c10,t12 and t10,c12 (29.0%); c9,t11 and t9,c11 (29.5%); c8,t10 and t8,c10 (12.3%); c11, c13 (0.96%); c10,c12 (0.88%); c9,c11 (0.88%); and c8,c10 (0.20%). As can be seen from these studies, even though the formation of certain isomers are favored, other isomers of CLA can contribute greatly to the composition of alkali isomerized CLA preparations.

In 1978, researchers at the University of Wisconsin discovered the identity of a substance contained in cooked beef that appeared to inhibit mutagenesis. This substance was found to be CLA. Fatty acids with conjugated unsaturation are not normally constituents of the cow's diet. However, c9,t11 octadecadienoic acid is formed in the rumen as a first intermediate in the biohydrogenation of linoleic acid by linoleic acid isomerase from the anaerobic bacterium Butyrivibrio fibrisolvens as reported by Kepler et al., J. Biol. Chem. 241:1350–54 (1966).

The biological activity of individual isomers of CLA has been the subject of some speculation. The literature generally suggests that the biologically active isomer is the c9,t11 isomer produced by Butyrivibrio fibrisolvens (for reviews adopting this position, see P. W. Parodi, J. Nutr. 127(6):1055–60 (1997), M. A. Belury, Nutrition Reviews 53(4): 83–9 (1995)). Further data supporting this assumption appears in Ha et al., Cancer Res., 50:1097 (1991). There, the researchers conducted labeled uptake studies which indicate that the 9,11 isomer appears to be somewhat preferentially taken up and incorporated into the phospholipid fraction of animal tissues, and to a lesser extent the 10,12 isomer.

The biological activity associated with CLA is diverse and complex. At present, very little is known about the mechanisms of action of CLA, although several preclinical and clinical studies in progress are likely to shed new light on the physiological and biochemical modes of action. The anti-carcinogenic properties of CLA have been well-documented. Administration of CLA inhibits rat mammary tumorigenesis, as demonstrated by Ha et al., Cancer Res., 52:2035-s (1992). Ha et al., Cancer Res., 50:1097 (1990), reported similar results in a mouse forestomach neoplasia model. CLA has also been identified as a strong cytotoxic agent against target human melanoma, colorectal and breast cancer cells in vitro. A recent major review article confirms the conclusions drawn from individual studies. (Ip, Am. J. Clin. Nutr. 66(6):1523s (1997)).

Although the mechanisms of CLA action are still obscure, there is evidence that some component(s) of the immune system may be involved, at least in vivo. U.S. Pat. No. 5,585,400 (Cook, et al.) discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.) disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066 describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.) discloses a method utilizing CLA as a dietary supplement in which pigs, mice, and humans were fed diets containing 0.5 percent CLA. In each species a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al.) provided data showing that incorporation of CLA into animal feed (birds and mammals) increased the efficiency of feed conversion leading to greater weight gain in the CLA supplemented animals.

The potential beneficial effects of CLA supplementation for food animal growers is apparent. What is needed is a determination of what the actual biologically active isomers are and the appropriate ratios in which these isomers should be utilized.

SUMMARY OF THE INVENTION

The scientific literature suggests that the active CLA isomer is the c9,t11 isomer. However, as shown herein, an enhanced ratio of 10,12 to 9,11 isomers has a pronounced effect on the biological activity of CLA preparations. Therefore, it is an object of the present invention to provide compositions containing CLA isomers in biologically favorable ratios. It is also an object of the present invention to provide methods for using compositions containing CLA isomers in biologically favorable ratios, and of biologically active isomers in enriched content for optimization of the desired biological effects.

Accordingly, in some embodiments, the present invention provides a conjugated linoleic acid composition comprising 10,12-linoleic acid and 9,11 linoleic acid, most preferably t10,c12 conjugated linoleic acid and c9,t11 conjugated linoleic acid, in a ratio of greater than 1.2:1, most preferably in a range of about 1.2:1 to 3:1. In other embodiments, the conjugated linoleic acid composition provided may also be part a daily ration for a human or animal diet. The daily ration comprises a vehicle having a liquid component. The liquid component contains or comprises 0.01 to 10 gram equivalents of 10,12 conjugated linoleic acid, preferably t10,c12 conjugated linoleic acid. Alternatively, in other embodiments, the invention provides a composition containing or comprising linoleic acid isomers, the isomers being characterized in containing or comprising a mixture of greater than 90 percent t10,c12 and c9,t11 CLA isomers. In some embodiments, the isomers are present in a ratio of about greater than 1.2:1 in favor of t10,c12.

In other embodiments, the invention also provides a conjugated linoleic acid composition containing or comprising at least 50 percent conjugated linoleic acid isomers. The CLA isomers may be characterized as containing greater than 90 percent of a mixture of t10,c12 and c9,t11 isomers. Preferably the ratio of these isomers is greater than 1.2:1 in favor of the t10,c12 isomer.

In other embodiments, the invention provides still other compositions and preparations enriched for t10,c12 CLA. In some embodiments, the t10,c12 CLA is at least approximately 80% pure, in other embodiments, the t10,c12 CLA is at least approximately 90% pure, and in still other embodiments, the t10,c12 CLA is at least approximately 92% pure.

In other embodiments, the invention provides compositions enriched for c9,t11 CLA for feeding to animals and other humans. In some embodiments, the ratio of c9,t11 CLA to t10,c12 CLA is from about 1.4:1 to 3.0:1. In other embodiments, the ratio of c9,t11 CLA to t10,c12 CLA is from about 1.8:1 to 2.2:1. In still other embodiments, the ratio of c9,t11 CLA to 10,c12 CLA is about 2.0:1.

The above compositions may incorporated into acylglycerides or alkylesters. In some embodiments, acylglycerol composition comprises a plurality of acylglycerol molecules of the structure:

wherein $R_1$, $R_2$, and $R_3$ are selected from the group consisting of a hydroxyl group and an octadecadienoic acid, the composition characterized in containing at least approximately 80% t10,c12 octadecadienoic acid at positions $R_1$, $R_2$, and $R_3$. In other embodiments, the acylglycerol composition is characterized in containing at least approximately 90% t10,c12 octadecadienoic acid at positions $R_1$, $R_2$, and $R_3$. In still other embodiments, the acylglycerol composition is characterized in containing at least approximately 92% t10, c12 octadecadienoic acid at positions $R_1$, $R_2$, and $R_3$. In other embodiments, the c9,t11 enriched CLA may be incorporated into positions $R_1$, $R_2$, and $R_3$ in the acylglycerol according to the ratios and percentages described above.

In further embodiments, the enriched t10,c12 compositions and enriched c9,t11 compositions may be incorporated into food products, including animal feeds and food for human consumption, or may be formulated with an excipient or oral delivery vehicle.

In other embodiments, the compositions of the present invention find a wide variety of nutritional, therapeutic and pharmacological uses. Compositions containing c9,t11 may be used to increase growth, feed efficiency and rate of gain. Accordingly, in some embodiments an animal and a composition enriched for c9,t11 CLA are provided. In some embodiments, the ratio of c9,t11 CLA to t10,c12 CLA is from about 1.4:1 to 3.0:1. In other embodiments, the ratio of c9,t11 CLA to t10,c12 CLA is from about 1.8:1 to 2.2:1. In still other embodiments, the ratio of c9,t11 CLA to 10,c12 CLA is about 2.0:1. In other embodiments, the enriched c9,t11 CLA composition comprises about 40–60% c9,t11 CLA and about 20–30% t10,c12 CLA. In other embodiments, the enriched c9,t11 preparation is administered to the animals so that feed conversion, growth or rate of gain are increased. Compositions containing t10,c12 CLA may be utilized to reduce body fat in humans and other animals. Accordingly, in some embodiments, an animal and a t10,c12 CLA composition are provided. In some embodiments, the t10,c12 CLA is at least approximately 80% pure, in other embodiments, the t10,c12 CLA is at least approximately 90% pure, and in still other embodiments, the t10,c12 CLA is at least approximately 92% pure. In still other embodiments, the t10,c12 preparation is administered to the animal, including humans, so that body fat is reduced. Other uses for these compositions include: increasing muscle mass in animals; attenuating allergic reactions in animals; preventing weight loss due to immune stimulation in animals; elevating CD-4 and CD-8 cell counts in animals; increasing the mineral content of bone in animals; preventing skeletal abnormalities in animals; and, decreasing the amount of cholesterol in the blood of animals.

In other embodiments, the present invention provides methods for producing t10,c12 CLA for commodity seed oils, including, but not limited to sunflower oil, safflower oil, soybean oil and corn oil. In some embodiments, a commodity seed oil and a method for treating the seed oil are provided. In other embodiments, the seed oil is treated under conditions such that a preparation comprising t10,c12 CLA is produced. In some embodiments, the CLA is at least approximately 80% t10,c12, in other embodiments, the CLA is at least approximately 90% t10,c12, and in still other embodiments, the CLA is at least approximately 92% t10, c12. In other embodiments, a mixture of alkylesters is formed from the commodity seed oil. In still other embodiments, the alkylesters are then conjugated. In some embodiments, the conjugated alkylesters are diluted in a solvent, and precipitated by lowering the temperature to at least about minus 56° C. to minus 57° C. In other embodiments, saturated fatty acids are removed from the preparation by lowering the temperature to about −30° C. In still other embodiments, the saturated fatty acids may be removed by urea fractionation. In other embodiments, the invention provides the t10, c12 CLA produced by the process just described.

DETAILED DESCRIPTION OF THE INVENTION

Definitions

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11,13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, it is intended that "triglycerides" of CLA contain CLA at any or all of three positions on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8,t10; c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

"Prepared food product" means any pre-packaged food approved for human consumption.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (including CLA) or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). Various uses of CLA have been well-documented in the patent and scientific literature. These uses may be divided into two general categories. The first category is the use of CLA nutritively as a dietary supplement. The second category is therapeutic and pharmacological uses.

U.S. Pat. No. 5,554,646 (Cook et al.), incorporated herein by reference, discloses the use of CLA for reducing body fat in animals. In this method, a safe and effective amount of CLA sufficient to cause reduction of body weight is fed to the animal. Mice fed a diet containing 0.5% CLA had a total fat content at the end of feeding that was significantly lower than the fat content of control mice fed a diet containing 0.5% corn oil. The exact amount of CLA to be administered to reduce body fat depends upon the animal, the form of CLA employed, and the route of administration. The amount generally ranges from about 0.001 g/kg to about 1 g/kg of the animal's body weight. Pharmaceutical amounts will generally range from about 1,000 parts per million (ppm) to about 10,000 ppm of CLA of the human's diet. However, the upper limit of the amount to be employed is not critical because CLA is relatively nontoxic. CLA for this and other uses may also be prepared in a variety of forms. These include nontoxic sodium or potassium salts of CLA in combination with a pharmaceutical diluent and active esters. CLA may also be incorporated directly into animal feed or food to be fed to a human so that CLA comprises approximately 0.01% to 2.0% or more by weight of the animal's or human's food. This patent also disclosed that supplementation of an animal's diet with CLA may serve to preserve body protein in an animal and to increase muscle protein in an animal.

Another nutritive use of CLA is disclosed in U.S. Pat. No. 5,428,072 (Cook et al.) incorporated herein by reference. There, feeding a safe and effective amount of CLA to animals is shown to enhance weight gain and feed efficiency in the animal. Groups of chicks fed a diet supplemented with 0.5% CLA demonstrated equivalent weight gain to control chicks fed 0.5% linoleic acid even though the CLA-fed chicks consumed less food. Furthermore, chicks fed 0.5% CLA and subsequently injected with endotoxin demonstrated weight gain, while chicks fed control diets either lost weight or gained very little weight. Similar results were seen in rats fed a diet containing 0.5% CLA and rabbits fed either 0.5% or 1% CLA. Guidelines for amounts of CLA to be fed or included in the diet are identical to those disclosed in U.S. Pat. No. 5,554,646.

Studies have also demonstrated that CLA may be used to actually reduce body weight in humans. In a double blind study conducted in Norway by Erling Thom in 1997, the diets of 20 healthy individuals were supplemented with either 3 gms of a CLA mixture or 3 gms of a placebo. The group fed CLA experienced both a decrease in body weight and body fat percentage while the group fed the placebo experienced an increase in body weight and body fat percentage. PCT Publication WO 97/46230 discloses a method for maintaining an existing level of body fat and/or body weight. The claims of that patent rely on an anecdotal, uncontrolled study wherein CLA was consumed by a total of 3 individuals.

Other patents on CLA use have focused on CLA's role in immune response. U.S. Pat. No. 5,585,400 (Cook et al.), herein incorporated by reference, discloses a method for attenuating allergic reactions in animals mediated by Type I or TgE hypersensitivity by administering a diet containing CLA. This patent also discloses administering CLA in concentrations of about 0.1 to 1.0% to preserve numbers of white blood cells. The studies disclosed in that patent utilized a guinea pig trachea allergy model. Guinea pigs were fed 0.25% CLA or control diets for two weeks, then immunized with ovalbumin on weeks two and three for hyperimmunization. A superfusion model system was used to determine if feeding CLA had any effect on the allergen-induced tracheal contraction. Tracheae from guinea pigs fed CLA were more stable in the superfusion system than tracheae of control-fed guinea pigs. When allergen was infused over the guinea pig trachea, less traecheic contraction was observed in the tissue of the CLA-fed animals. The white blood cell count of animals fed CLA was elevated as compared to control animals, the CLA-fed animals having a white blood cell count of $3.5 \times 10^6 +/- 0.6$ as compared to $2.4 \times 10^6 +/- 0.3$ for the control animals.

The use of CLA to enhance growth and prevent anorexia and weight loss due to immune stimulation (e.g., endotoxin exposure) and the adverse effects of catabolic hormones (e.g., IL-1) was disclosed in U.S. Pat. No. 5,430,066 (Cook, et al.), herein incorporated by reference. Chicks fed a diet of 0.5% CLA and subsequently challenged by endotoxin injection exhibited weight gain while chicks fed a control diet failed to gain weight following endotoxin exposure. Similar results were obtained in rats fed a diet containing 0.5% CLA as compared to animals fed a control diet of 0.5% corn oil. Preparations and dosage ranges disclosed were identical to those disclosed in U.S. Pat. No. 5,554,646.

Methods of treating animals to maintain or elevate CD-4 and CD-8 cell levels and to prevent or alleviate the adverse effects on the animal caused by the production or exogenous administration of tumor necrosis factor (TNF) or by a virus consisting of administering to the animal a safe and effective amount of CLA were disclosed in U.S. Pat. No. 5,674,901 (Cook et al.), herein incorporated by reference. Mice were fed either a control diet or 0.5% CLA and subsequently challenged with injections of TNF. Mice fed CLA lost less weight than the control mice. Likewise, chicks fed a 0.5% CLA diet and subsequently challenged with a wing web injection of live attenuated fowl pox virus gained more weight than chicks fed a control diet. Chicks fed the 0.5% CLA diet demonstrated a markedly enhanced percent of CD-4 and CD-8 cells as compared to chicks fed a control diet.

European Patent Application 779,033 A1 (Lievense, et al.), herein incorporated by reference, discloses the use of CLA for improving blood lipid profile. Briefly, hamsters were fed diets containing CLA incorporated into a triglyceride in the form of a fat spread at a rate of 1.5% of the total calories of their diet. Hamsters fed CLA exhibited a decrease in total cholesterol, a decrease in HDL cholesterol, and decrease in LDL cholesterol.

CLA has also been demonstrated to affect bone deposition, as reported in PCT Publications WO 98/05318 (Cook, et al.), and WO 98/05319 (Cook, et al.), both incorporated herein by reference. Chicks fed a diet containing 0.1875%, 0.375%, or 0.75% of the diet, exhibited a substantial decrease in skeletal abnormalities as compared to chicks receiving no CLA in their diet. Furthermore, chicks fed a diet containing 0.5% CLA exhibited on increase in bone mineral content.

Other patents describe various formulations of CLA. European Patent Application EP779033 A1 discloses an edible fat spread containing 0.05 to 20% (by weight) conjugated linoleic acid residues. There, a commercially-available mixture of free fatty acids having a linoleic acid content of 95.3% was subjected to alkali isomerization with NaOH in ethylene glycol. The free fatty acids were incorporated into triglycerides by mixing with 10 parts palm oil and lipase. The mixture was stirred for 48 hours at 45° C. and the lipase and free fatty acids removed. Seventy parts of this composition and 29 parts water, 0.5 parts whey protein powder, 0.1 parts salt, and a small amount of flavor and citric acid (to obtain a pH of 4.5) were combined and processed to produce a fat spread.

Other foods containing a safe and effective amount of CLA are disclosed in PCT Publication WO 97/46118 (Cook, et al.), herein incorporated by reference. There, a liquid dietetic food for parenteral administration to humans containing emulsified fat particles of about 0.33–0.5 micrometers in diameter is disclosed. The emulsion contains 0.5 mg/gm to 10 mg/gm of CLA or alternatively, 0.3% to 100% CLA based on the food lipid or 0.03 gm to 0.3 gm CLA per 100 calorie serving. This application also discloses a baby formula containing similar amounts of CLA along with 2.66 gm of protein, 5.46 gm of fat, 10.1 gm of carbohydrate, 133 gm of water, and vitamins and minerals in RDA amounts. Another example of a low-residue liquid enteral dietetic product useful as a high-protein, vitamin and mineral supplement is disclosed. This supplement contains CLA at 0.05% to about 5% by weight of the product, or by 0.3% to about 100% of the lipid present or about 0.03 to 0.3 gm CLA per 100 calories. Additionally, 140 calories of a representative formula can contain 7.5 gm of egg white solids, 0.1 gm CLA, 27.3 gm carbohydrate such as sucrose or hydrolyzed cornstarch, 1.9 gm of water, and vitamins and minerals in RDA amounts.

In the present invention, preparations enriched for either the 10,12 isomer or 9,11 isomers are preferably utilized for each of the applications described above. Enriched preparations of the 9,11 isomer are available commercially from Matreya (State College, Pa.). CLA preparations enriched for the t10,c12 isomer may preferably be prepared by preparative scale gas chromatography or by the precipitation method presented in Example 4.

The Inventors have discovered, contrary to most current scientific opinion, that a particularly active CLA isomer may actually be the t10,c12 isomer of CLA. In the present invention, the ratio of 10,12 to 9,11 isomers, most preferably the ratio of t10,c12 to c9,t11 isomers, added to human food supplements and animal feeds is controlled to provide desirable nutritional, therapeutic and pharmacologic effects. The ratio of 10,12 to 9,11 isomers, most preferably the ratio of the t10,c12 to c9,t11 isomers, utilized is about greater than 1.2:1, most preferably between about 1.2:1 to 3:1. Because CLA is non-toxic, the upper limit of the ratio of the 10,12 to 9,11 isomers is not important. However, it is expected that exceeding the 3:1 ratio threshold will result in relatively minor additional benefit; however, delivery of enriched 10,12 CLA will be efficacious at levels that exceed its maximum observed effect.

The compositions of the present invention are preferably formulated by combining an enriched preparation of the t10,c12 isomer with either an enriched preparation of the 9,11 isomer or a normal CLA preparation produced by alkali isomerization. In each case, the enriched preparation of the 10,12 isomers is added so that the desired ratio of 10,12 to 9,11 isomers is achieved. The isomer composition of the various CLA preparations may preferably be confirmed by gas chromatography, as is known in the art.

Alternatively, the 10,12 isomers may be provided as a daily ration in a vehicle with a lipid component containing or comprising 0.01 to 10 gram equivalents of the 10,12 isomers, most preferably 0.01 to 10 gram equivalents of the t10,c12 isomer. Gram equivalents means that the total amount of 10,12 isomers provided, irrespective of other isomers present, is from 0.01 to 10 grams. The amount of 10,12 isomer present may be that amount which results in a 10,12 to 9,11 ratio of about greater than 1.2:1. When the 10,12 isomers are provided as part of a daily ration, the intake may occur in a single dose, or as a series of doses in a feed or various food products consumed throughout the day.

The compositions of the present invention may also take the form of a bulk product for sale in commerce. The bulk CLA product contains or comprises at least 50 percent conjugated linoleic acid isomers. The linoleic acid isomers may be characterized in containing greater than 90 percent of a mixture of t10,c12 and c9,t11 isomers. Preferably these isomers are provided in a ratio of greater than about 1.2:1 in favor of t10,c12, most preferably in a range of about 1.2:1 to 3:1. This bulk product may be diluted into nutritional products such as animal feeds, human dietary supplements, and human food products. Those products will be compositions containing or comprising linoleic acid isomers characterized in containing greater than 90 percent of a mixture of t10,c12 and c9,t11 isomers. Preferably these isomers are provided in a ratio of greater than about 1.2:1 in favor of t10,c12, most preferably in a range of about 1.2:1 to 3:1.

The compositions of the present invention will have a variety of uses. These uses include: the reduction of body fat in animals; increasing muscle mass in animals; increasing feed efficiency in animals, reducing body weight in humans, attenuating allergic reactions in animals; preventing weight loss due to immune stimulation in animals; elevating CD-4 and CD-8 cell counts in animals; increasing the mineral content of bone in animals; preventing skeletal abnormalities in animals; and, decreasing the amount of cholesterol in the blood of animals. In each case, the term animal includes all mammals including humans. The preferred dosages and ratios of the 10,12 isomers, most preferably the t10,c12 isomer, utilized for each application are the same as described above.

In a preferred embodiment of the present invention, a safe and effective nutritional or therapeutic amount of t10,c12 CLA is orally administered to an animal (including humans) to decrease body weight or fat. In some embodiments, the t10,c12 CLA is at least approximately 80% pure, in other embodiments, the t10,c12 CLA is at least approximately 90% pure, and in still other embodiments, the t10,c12 CLA is at least approximately 92% pure. t10,c12 CLA may be administered to obese and non-obese humans. Because t10,c12 CLA is a non-toxic, naturally occurring food ingredient and not a drug, t10,c12 CLA may be consumed as a part of a normal diet and finds use as a part of everyday nutrition in people without obesity. A nutritionally effective amount is that amount t10,c12 CLA that, when ingested in purified form or as food supplement results in a reduction in body weight or fat without impairing or interfering with proper nutrition. Accordingly, administration of a nutritionally effective amount of t10,c12 CLA achieves weight loss without sensory deprivation associated with reduction in food intake. t10,c12 CLA may also be used to treat humans with slight to profound clinical obesity. When treating humans with clinical obesity, a therapeutically effective amount of t10,c12 CLA is administered. A therapeutically effective amount is that amount which causes a reduction in weight or body fat of a clinically obese person. In the present invention, about 0.1 to 15 grams of CLA may be administered per day, preferably about 0.1 to 5 grams per day may be administered and most preferably about 1.8 grams per day may be administered. In general, the amount of CLA administered is not critical as long as it is enough to be nutritionally or therapeutically effective. The amounts of CLA deemed nutritionally or therapeutically effective are those which result in measurable weight or fat loss when administered over a four week period or longer.

It is anticipated that there will be some variation in effectiveness because of differences among individuals in parameters such as body weight, basal metabolism, exercise, and other aspects of the diet. The individual should begin with the preferred 1.8 gram dose for an initial two week period, and then, if no weight loss is experienced, gradually increase the CLA dose up to about 10–15 grams per day.

The present invention also contemplates the use of derivatives of the isomer-enriched preparation of CLA. For example, CLA may be free or bound through ester linkages or provided in the form of an oil containing isomer enriched CLA triglycerides, as described in Example 5. In these embodiments, the triglycerides may be partially or wholly comprised of isomer enriched CLA attached to a glycerol backbone. The isomer enriched CLA may also be provided as a methylester or ethylester, as described in the examples. Furthermore, the isomer enriched CLA may be in the form of a non-toxic salt, such as a potassium or sodium salt (e.g., a salt formed by reacting chemically equivalent amounts of the free acids with an alkali hydroxide at a pH of about 8 to 9).

In some preferred embodiments, administration is oral. The isomer enriched CLA may be formulated with suitable carriers such as starch, sucrose or lactose in tablets, pills, dragees, capsules, solutions, liquids, slurries, suspensions and emulsions. The isomer enriched CLA may be provided in aqueous solution, oily solution, as or in any of the other forms discussed above. The tablet or capsule of the present invention may be coated with an enteric coating which dissolves at a pH of about 6.0. to 7.0. A suitable enteric coating which dissolves in the small intestine but not in the stomach is cellulose acetate phthalate. In a preferred formulation, the isomer enriched CLA is provided as soft gelatin capsules. The isomer enriched CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

The isomer enriched CLA may also be provided as a supplement in various prepared food products and drinks. For the purposes of this application, prepared food product means any natural, processed, diet or non-diet food product to which isomer enriched CLA has been added. The isomer enriched CLA may be added in the form of free fatty acids or as an oil containing partial or whole triglycerides of isomer enriched CLA. Therefore, isomer enriched CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods.

CLA is also susceptible to oxidation. Therefore it is desirable to package isomer enriched CLA for human use with suitable antioxidants such as lecithin, tocopherols, ascorbate, ascorbyl palmitate or spice extracts such as rosemary extract.

Currently, most CLA is manufactured by the alkali isomerization process. An oil containing a high amount of linoleic acid such as sunflower oil, evening primrose oil or safflower oil is reacted in an inert nitrogen environment with potassium hydroxide and a solvent such as propylene glycol at about 180° C. for about 2.5 hours. The reaction product is acidified and washed several times with acidic water and finally dried under vacuum. For a complete description of the laboratory scale production of CLA by alkali isomerization, see U.S. Pat. No. 5,554,646, incorporated herein by reference. CLA may also be produced by the continuous flow alkali isomerization process described in U.S. Pat. No. 4,164,505, incorporated herein by reference. The reaction product obtained from these processes is a mixture of CLA, linoleic acid and the other fatty acids found in the source oil. Generally, the amount of CLA derived from alkali isomerization of sunflower oil is about 60% of the total free fatty acid product and contains approximately equal amounts of the c9,t11 and t10,c12 isomers.

Another method of producing a preparation consisting of primarily cis-9, trans-11 CLA is disclosed in U.S. Pat. No. 5,674,901, incorporated herein by reference. In that method, linoleic acid containing oil is incubated with the microorganism *Butyrivibrio fibrisolvens*. *B. fibrisolvens* contains an $\Delta^{12}$-cis,$\Delta^{11}$-isomerase which converts linoleic acid into cis-9, trans-11 CLA.

EXAMPLES

Example 1

Three different studies have been conducted which examine the relationship between CLA content in feed and the amount of back fat in hogs. In a study conducted at Iowa State University and reported at the Midwest Animal Science meetings, R. L. Thiel et al. reported that pigs fed CLA experience a reduction in back fat. Briefly, eight replications of five littermate barrows with an average initial weight of 26.3 kg were allotted randomly to individual pens. The pigs were fed for an average of 93 days and had an average weight of 116 kg at slaughter. The group fed a diet of 0.5% CLA experienced a 10.3% decrease in back fat. Although not initially published, the CLA utilized in the diets contained a ratio of 10,12 to 9,11 isomers of CLA of 1.05:1.

In another study conducted by researchers at Kansas State University and reported at the Midwest Animal Science Meetings, 36 crossbred barrows with an average initial weight of 83 lbs. were fed a diet containing 0.50% CLA. The average ending weight was approximately 230 lbs. The barrows fed diets containing CLA experienced a 7.2% decrease in back fat. The ratio of 10,12 to 9,11 isomers of CLA in the CLA utilized in this experiment was 0.487:1.

In another study, as yet unpublished, 24 barrows with a beginning weight of 26 kg were fed a diet containing 0.48% CLA or a control diet. The hogs were fed to an ending weight of 118 kg. Hogs fed CLA experienced a 13.7% decrease in back fat. The ratio of 10,12 to 9,11 isomers of CLA in this experiment was 1.16:1.

Figure 1:
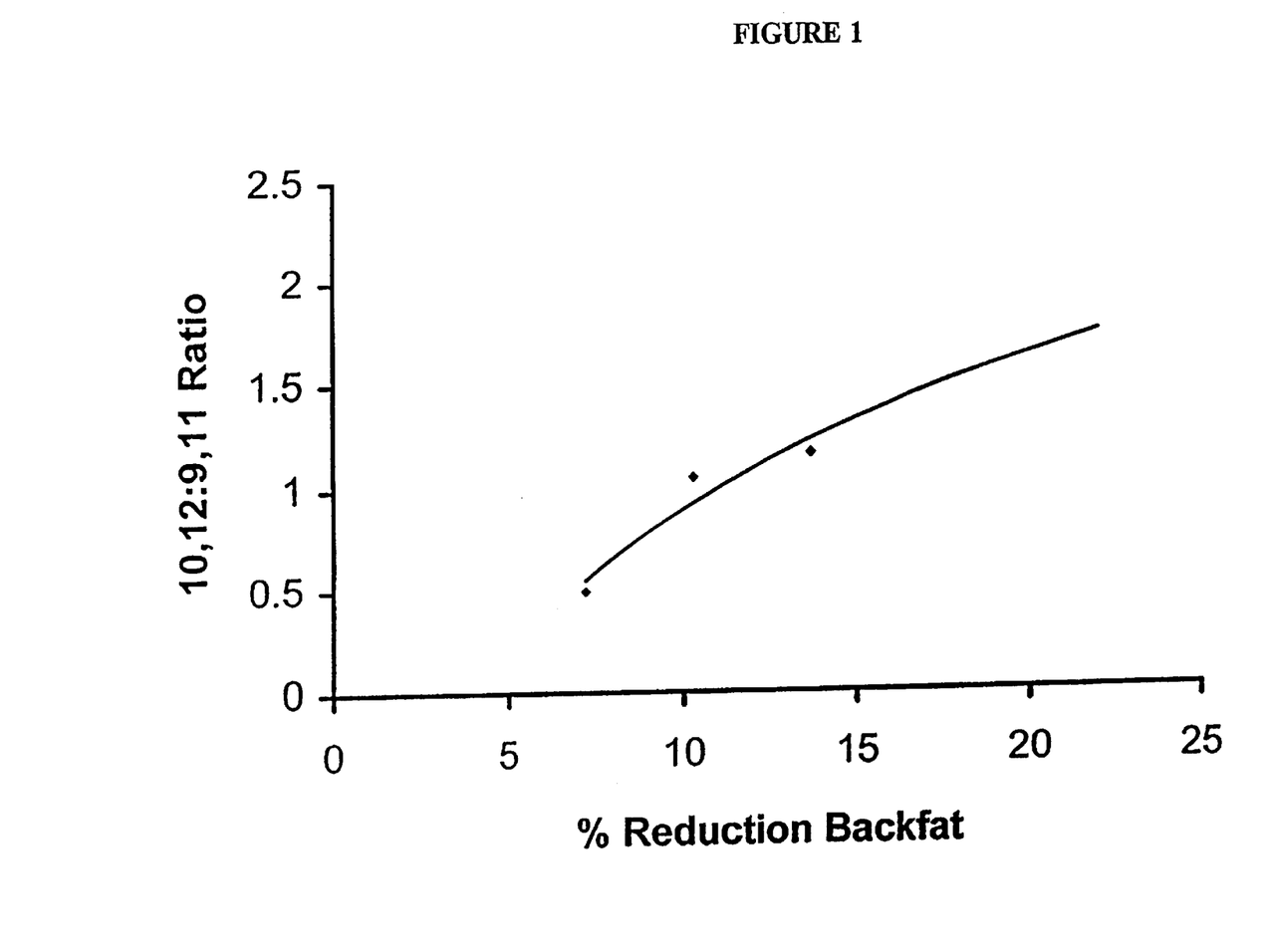
FIG. 1 is a plot of a logarithmic regression analysis of three separate studies comparing the ratio of the 10,12 and 9,11 isomers of CLA to percent reduction back fat in hogs.

The ratio of 10,12 to 9,11 isomers of CLA utilized in each of these studies was plotted against percent reduction back fat and analyzed by logarithmic regression. The results are presented in FIG. 1. These results indicate that as the ratio of 10,12 to 9,11 isomers of CLA increases, the percent reduction in back fat also increases. Therefore, preparations of CLA containing a ratio of 10,12 to 9,11 of greater than about 1.2:1 are desirable.

Figure 2:
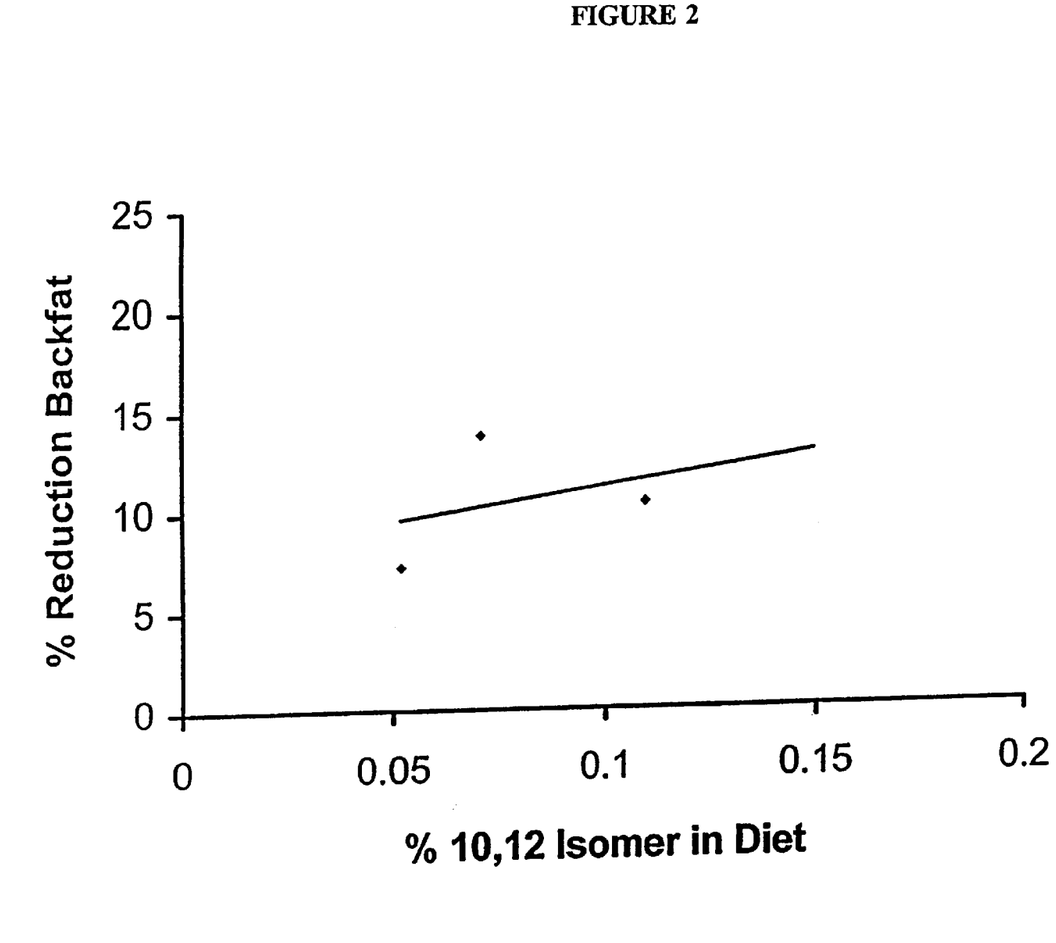
FIG. 2 is a plot of a linear regression analysis of three separate studies comparing the total percentage of the 10,12 isomer of CLA in the diet of hogs to percent reduction back fat.

The total amount of 10,12 isomers in the diet may also effect back fat deposition. The percent of 10,12 isomers in the diets was plotted against percent reduction back fat and analyzed by linear regression. The results are presented in FIG. 2. These results demonstrate that as the total amount of 10,12 isomers in the diet increases, back fat is reduced. The effect seen is not as great as for isomer ratio. However, these results may be consistent with the ratio results. The studies relied upon did not differentiate between isomers. It is possible that the amounts and ratios of the 9,11 and other isomers present masked any effect relating to the increasing percentage of 10,12 in the diet. When a preparation of CLA enriched for the 10,12 isomer is utilized, it is expected that the results will be comparable to the ratio results.

Example 2

The scientific literature indicates that either the biologically active isomers of CLA have not been identified, or that c9,t11 CLA is the biologically active isomer. Based on the results of Example 1, the Inventors believe that the t10,c12 isomer is an active isomer. Therefore, the effect of feeding different ratios and amounts of CLA isomers to mice is examined to demonstrate that the t10,c12 isomer is a biologically active isomer and that the ratio of t10,c12 to c9,t11 may be manipulated to produce desirable biological effects.

The trial was conducted with 84 ICR mice purchased from Harlan Sprague Dawley (Madison, Wis.). The diets were blended using the basal diet, sugar, corn oil and one or a blend of isomers of conjugated linoleic acid (expressed as percent of diet). Each treatment consisted of 2 pens of 3 mice. Mice had food and water ad libitum. Food consumption was monitored daily and mice were weighed every other day when bedding was changed. At three weeks of feeding the diet, mice were euthanized by $CO_2$ and final body weights were taken. Mice were then necropsied and fat pads were weighed. Mice were also analyzed for total body fat. Mice were freeze dried and ground. Duplicate samples were analyzed by proximate analysis (ether extraction, ash, kjeldahl, and moisture). The results are reported in Table 1.

TABLE 1

| Treatment 9, 11%: 10, 12% | Gain (g) | Feed Consumption 0–3 weeks (g) | Feed Conversion 0–3 weeks | % Fat |
|---|---|---|---|---|
| 0.0:0.0 | 9.88 | 85.75 | 8.75 | 13.995 |
| 0.0:0.1 | 9.38 | 87.67 | 9.34 | 8.806 |
| 0.0:0.2 | 8.88 | 81.72 | 9.73 | 6.439 |
| 0.0:0.4 | 9.35 | 83.27 | 8.97 | 3.003 |
| 0.1:0.0 | 9.77 | 86.58 | 8.87 | 9.880 |
| 0.2:0.0 | 11.38 | 92.83 | 7.02 | 10.346 |
| 0.4:0.0 | 11.55 | 88.62 | 7.86 | 13.403 |
| 0.1:0.1 | 10.49 | 92.38 | 8.89 | 9.560 |
| 0.1:0.2 | 8.17 | 82.98 | 10.28 | 7.306 |
| 0.2:0.0 | 11.38 | 92.83 | 7.02 | 10.346 |
| 0.2:0.1 | 11.23 | 89.43 | 8.49 | 7.922 |
| 0.2:0.2 | 8.75 | 79.82 | 9.15 | 7.115 |
| 0.2:0.4 | 10.23 | 88.20 | 8.64 | 3.088 |
| 0.4:0.0 | 11.55 | 88.62 | 7.86 | 13.403 |
| 0.4:0.2 | 9.50 | 85.27 | 8.98 | 7.508 |
| 0.4:0.4 | 9.97 | 81.57 | 8.19 | 0.476 |

Mice fed only c9, t11 CLA showed a linear improvement in growth (16%) when no t10, c12 was present. The opposite was true with the t10, c12 isomer, where there was a 10% reduction in growth. As a result c9, t11 also increased consumption by 8% at the ratio of 0.2%:0%. These data also indicate that increased amounts of the t10,c12 isomer in the diet causes a reduction in body fat. When compared to control mice not receiving CLA in the diet, mice fed only t10,c12 CLA had reduced body fat and reduced growth. In contrast, mice receiving only c9,t11 CLA demonstrated increased growth, rate of gain, and feed conversion. When mice were fed both t10,c12 and c9,t11 CLA, body fat decreased with increasing t10,c12. It was found that the optimum ration for improving growth, feed conversion and reducing fat is about approximately 2:1 c9,t11:t10,c12. These data indicate that the different CLA isomers have different biological effects.

Example 3

A preparation of CLA enriched for the 10,12 isomer was prepared by preparative scale gas chromatography. The resulting product was analyzed by gas chromatography. For recent descriptions of gas chromatography methods for identifying CLA isomers, see Christie et al., *JAOCS* 74(11):1231 (1997), Christie et al., *Lipids* 33(2): 217–21 (1998), Sehat et al., *Lipids* 33(2):217–21 (1998), and Marcel S. F. Lie Ken Jie and J. Mustafa, *Lipids* 32 (10): 1019–34 (1997). The foregoing references are herein incorporated by reference. The gas chromatography conditions were as follows:
System: Perkin-Elmer Auto System
Injector: Splitless at 240° C.
Detector: Flame Ionization Detector at 280° C.
Carrier: Helium
Column: WCOT Fused Silica 0.25 mm ×100M, CP-SL 88 for FAME, DF 0.2
Oven Program: 80° C. (0 min.) increasing to 220° C. at 10° C. per min. and held at 220° C. for 10 min.
All results are expressed as the relative peak area percentage. The results of the analysis were:

| Isomer | Area(%) |
|---|---|
| C16:0 | 2.01 |
| C18:0 | 0.57 |
| C18:1 | 0.26 |
| c9, t11 | 1.61 |
| t10, c12 | 92.75 |
| t9, t11; t10, t12 | 1.16 |
| Unidentified | 1.64 |
| Total | 100.0 |

Example 4 t10,c12 CLA may be produced in larger quantities by an alternative method. Fully refined sunflower (safflower oil may be substituted) is used a the raw material. Ethylesters are formed by adding excess pure ethanol containing 1% sodium-ethylate as a catalyst to the oil. The mixture is heated to 60° C. for 30 minutes while stirring and allowed to separate. The bottom layer is drained off and the top layer is washed with slightly acidic water and dried under vacuum.

The ethylester mixture is then purified by molecular distillation at 160° C. and $10^{-2}$ mbar pressure, and the residue is discarded. Conjugation is performed by adding 0.5–1% of ethanol and 0.5–1% of potassium ethylate to the ethyl ester and agitating the mixture at 120° C. for 1 hour. The reaction is stopped by adding dilute citric acid. The oil is then washed and dried.

The conjugated ethylester is then diluted in acetone and cooled to −30° C. and filtered to remove most of the saturated fatty acids. The filtrate is then further cooled to −56 to −57° C. to allow the t10,c12 ethylester to precipitate. The ethylester is obtained by removing the acetone from the precipitate by applying a vacuum with slight warming. The t10,c12 ethylester so obtained is at least about 90% pure. If higher purity is desired, additional saturated fat may be removed from the ethylester prior to conjugation. This may be accomplished by urea fractionation. The resulting product is at least about 97% t10,c12 after the final precipitation.

Free fatty acids are produced from the ethylesters by saponification followed by neutralization. To saponify, a 10% amount of water containing ethanol to improve solubility and 100% excess of NaOH are added to the alkylesters to form a soap. The reaction is performed at 70° C. Then, the soap is diluted with water and HCl added to make the overall mixture acidic while stirring well. The free fatty acids separate to form a top layer and are washed with diluted citric acid and finally dried. The results were analyzed by gas chromatography as described above. The results using urea fractionation were:

| Isomer | Area(%) |
|---|---|
| c9, t11 | 1.80 |
| t10, c12 | 97.49 |
| t9, t11; t10, t12 | 0.71 |
| Total | 100.0 |

Results without urea fractionation were:

| Isomer | Area(%) |
|---|---|
| C16:0 | 1.75 |
| C18:2, c9, c12 | 0.16 |
| C18:1, c9 | 2.22 |
| c9, t11 | 6.36 |
| t10, c12 | 88.84 |
| t9, t11; t10, t12 | 0.23 |
| c9, c11; c10, c12 | 0.15 |
| Unidentified | 1.64 |
| Total | 100.0 |

Example 5

Triacylglycerols of CLA can be prepared by direct esterification. Immobilized *Candida antarctica* lipase (1.25 g) is added to a mixture of glycerol (1.22 g. 13.3 mmol) and isomer enriched (enriched either for t10,c12 or c9,t11) CLA as free fatty acid (M.wt. 280.3 g/mol; 11.6 g, 41.5 mmol). The mixture is gently stirred on a magnetic stirrer hot plate at 65° C. under continuous vacuum of 0.01–0.5 Torr. The volatile water produced during the progress of the reaction is continuously condensed into liquid nitrogen cooled traps. After 48 h the reaction is discontinued, n-hexane added and the enzyme is separated off by filtration. The organic phase is treated with an alkaline aqueous solution of sodium carbonate to remove excessive free fatty acids (when required). The organic solvent (after drying over anhydrous magnesium sulfate when appropriate) is removed in vacuo on a rotary evaporator followed by high-vacuum treatment to afford the virtually pure product as a slightly yellowish oil. When stoichiometric amounts of free fatty acids are used, titration by standardized sodium hydroxide is applied to determine the free fatty acid content of the crude reaction product (less than 1% free fatty acid content as based on number of mol of ester groups, corresponding to at least 99% incorporation, which is equivalent to the minimum of 97% triglyceride content). The crude product is directly introduced into HPCL eluting with 10% diethylether in n-hexane to afford 100% pure triglyceride as a colourless oil.

In order to monitor the progress of the reaction and provide more details about the composition of individual glycerides during the reaction, samples are collected regularly as the reaction proceeds. They are analyzed by HNMR spectroscopy and provide a good insight into the composition of mono-, di- and triacylglycerols during the progress of the reaction.

Example 6

This example describes the large scale batch production of conjugated safflower FAME (fatty acid methyl esters). The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of $NaOCH_3$ (30% solution) were added. The mixture was heated to 65° C. while stirring, and reacted at 65° C. for 2 hours. The resulting bottom layer was decanted while the reactor is purged with nitrogen gas. 1000 liters of water (40–50° C., into which 50 kg citric acid monohydrate has been dissolved) was then added while stirring. The layers are allowed to separate (approx. 60 min.) and the bottom layer decanted while purging the reactor with nitrogen gas. The resulting safflower FAME product is dried at 80° C. under vacuum for one hour. The resulting safflower FAME product can be conjugated and enriched for either t10,c12 CLA or c9,t11 CLA as described above.

What is claimed is:

1. A composition comprising an excipient and a conjugated linoleic acid component, said conjugated linoleic acid component comprising greater than about 92% of the t10, c12 isomer of conjugated linoleic acid.

2. The composition of claim 1, wherein said t10,c12 isomer is provided as an ester.

3. The composition of claim 1, wherein said t10,c12 isomer is provided a triglyceride.

4. The composition of claim 1, wherein said excipient is selected from the group consisting of starch, sucrose, and lactose.

5. The composition of claim 1, further comprising about 0.01 to 10 gram equivalents of said t10,c12 isomer of conjugated linoleic acid.

6. A composition comprising a capsule, said capsule containing a conjugated linoleic acid component comprising greater than about 92% of the t10,c12 isomer of conjugated linoleic acid.

7. The composition of claim 6, wherein said t10,c12 isomer is provided as an ester.

8. The composition of claim 6, wherein said t10,c12 isomer is provided as a triglyceride.

9. The composition of claim 6, wherein said capsule has an enteric coating.

\* \* \* \* \*